US011253383B2

(12) United States Patent
Hanft

(10) Patent No.: US 11,253,383 B2
(45) Date of Patent: Feb. 22, 2022

(54) CAM WALKER WITH REMOVABLE COLLAR

(71) Applicant: LEG DEFENDER, LLC, South Miami, FL (US)

(72) Inventor: Jason R. Hanft, South Miami, FL (US)

(73) Assignee: Foot Defender LLC, South Miami, FL (US)

( * ) Notice: Subject to any disclaimer, the term of this patent is extended or adjusted under 35 U.S.C. 154(b) by 430 days.

(21) Appl. No.: 16/136,722

(22) Filed: Sep. 20, 2018

(65) Prior Publication Data

US 2020/0093625 A1 Mar. 26, 2020

(51) Int. Cl.
*A61F 5/01* (2006.01)
*A61H 3/00* (2006.01)

(52) U.S. Cl.
CPC .......... *A61F 5/0111* (2013.01); *A61F 5/0195* (2013.01); *A61H 3/00* (2013.01)

(58) Field of Classification Search
CPC .......... A43B 7/20; A43B 7/14; A43B 5/1691; A43B 3/242; A61F 5/01; A61F 5/0111; A61F 5/0127; A61F 5/0195; A61F 5/0585; A61F 5/0113; A61F 2005/0167; A61F 13/066; A61F 13/043; A61F 13/045; A61H 3/00
USPC ....... 602/5, 12, 23, 27, 28, 62, 65; 128/882; 36/83, 85, 88–89, 101, 110
See application file for complete search history.

(56) References Cited

U.S. PATENT DOCUMENTS

| 5,078,128 | A | | 1/1992 | Grim |
| 5,317,820 | A | | 6/1994 | Bell et al. |
| 5,368,551 | A | | 11/1994 | Zuckerman |
| 5,400,529 | A | * | 3/1995 | Bell ........................ A43B 5/00 36/114 |
| 5,425,701 | A | | 6/1995 | Oster et al. |
| 5,571,078 | A | | 11/1996 | Malewica |
| 6,409,695 | B1 | | 6/2002 | Connelly |
| 7,303,538 | B2 | | 12/2007 | Grim et al. |
| 7,524,295 | B1 | | 4/2009 | Peters et al. |
| 9,180,038 | B2 | | 11/2015 | Ingimundarson et al. |
| 2007/0293798 | A1 | | 12/2007 | Hu |
| 2009/0227927 | A1 | | 9/2009 | Frazer |
| 2009/0287127 | A1 | | 11/2009 | Hu et al. |
| 2009/0287128 | A1 | * | 11/2009 | Ingimundarson ..... A61F 5/0102 602/27 |
| 2013/0018294 | A1 | | 1/2013 | Jones |
| 2014/0276301 | A1 | | 9/2014 | Grim et al. |

(Continued)

FOREIGN PATENT DOCUMENTS

EP 1227774 B1 3/2003

OTHER PUBLICATIONS

International Search Report, dated Jan. 31, 2020.

*Primary Examiner* — Caitlin A Carreiro
(74) *Attorney, Agent, or Firm* — Richard P. Gilly, Esquire; Archer & Greiner, P.C.

(57) ABSTRACT

A CAM walker includes a removable collar assembly configured to engage a cast or other brace device being worn on a lower extremity received in the walker. The collar assembly includes portions, such as paddles, configured to be brought into engagement with the brace device sufficiently to inhibit anterior and posterior movement of the proximal end of the walker relative to the proximal end of the lower extremity received therein.

15 Claims, 10 Drawing Sheets

(56) References Cited

U.S. PATENT DOCUMENTS

| | | |
|---|---|---|
| 2014/0316316 A1 | 10/2014 | Andrews et al. |
| 2015/0164179 A1 | 6/2015 | Walborn et al. |
| 2016/0045354 A1 | 2/2016 | Lee et al. |
| 2016/0213506 A1 | 7/2016 | Chen |
| 2016/0324666 A1 | 11/2016 | Barberio |
| 2017/0165093 A1 | 6/2017 | Huttenlocker et al. |

\* cited by examiner

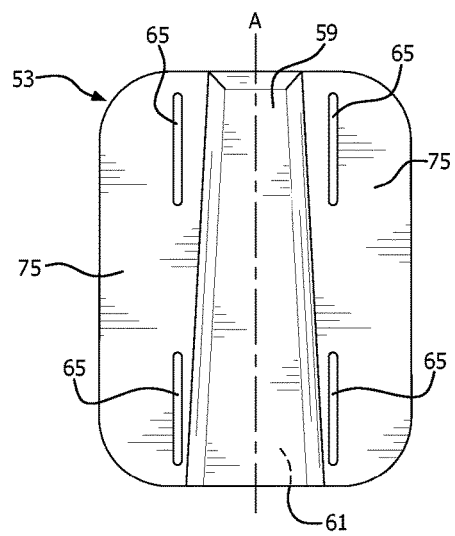
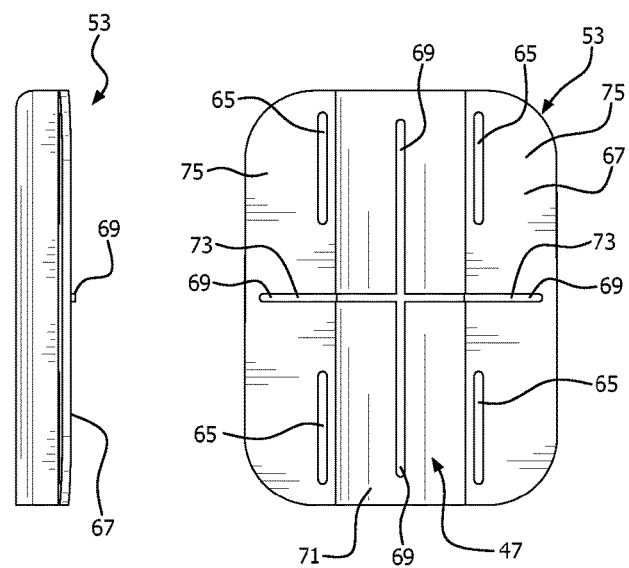
FIG. 3  FIG. 4  FIG. 5

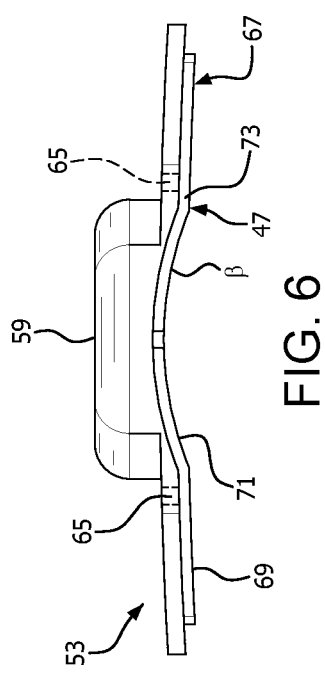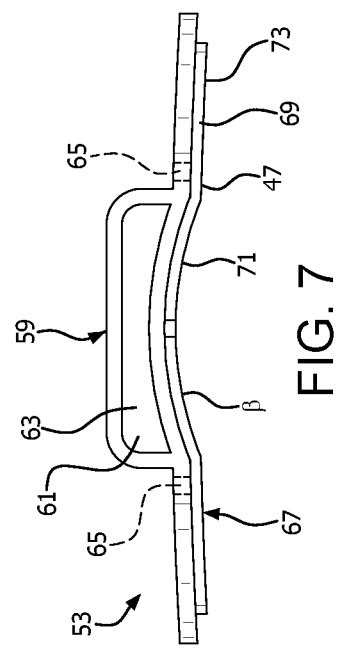

CAM WALKER WITH REMOVABLE COLLAR

FIELD

This disclosure relates to lower extremity walkers and, in particular, to walkers for use with brace devices.

BACKGROUND

CAM walkers, that is, "Controlled Ankle Movement" walkers, are available in a variety of shapes and sizes. Among their purposes, such leg walkers immobilize the ankle joint, protect portions of the lower extremity, or otherwise treat or address a variety of conditions of the lower extremity.

While certain CAM walkers may include panels or portions to increase or decrease the leg height of such walkers, such designs suffer from various drawbacks and disadvantages. For example, adjustable-height walkers are often complex to manipulate or otherwise not suited to various lower extremity treatment protocols, such as when lower extremities are casted.

Devices which may be associated for use with rigid or semi-rigid casted lower extremities may also suffer from various drawbacks and disadvantages, including their limited application and disadvantageous offloading or other therapeutic characteristics.

Due to the limited adaptability and other drawbacks of CAM walkers of the current art, medical practitioners, hospitals, and other care centers are often required to "double up" on CAM walkers, or otherwise stock and make use of discreet CAM walkers for different treatment phases or lower extremity conditions, thereby causing excess inventory and wasteful inefficiency in the healthcare system in general, and to patients and care providers in particular.

Accordingly, it would be desirable to address the foregoing drawbacks and disadvantages with an improved leg walker, such as a Controlled-Ankle-Movement (CAM) walker.

SUMMARY

In accordance with one possible implementation of the present disclosure, a CAM walker, is configured so as to be suitable for use with another brace device on the lower extremity received in the CAM walker. As used herein, the terms CAM walker and walker may be used interchangeably and either of such terms shall broadly mean any number of boots, walkers, or other lower extremity footwear for controlling or limiting relative movements of a lower extremity, protecting or isolating such lower extremity, or achieving other therapeutic goals related to the lower extremity. The terms distal and proximal, anterior and posterior, medial and lateral, shall be in reference to a standing individual.

As such, the CAM walker may include a frame which controls ankle movement of the lower extremity. The frame, when worn, has a distal frame end at or near the foot and a proximal frame end generally above the ankle, each frame end adapted to operatively engage, whether directly or indirectly, portions of the foot and calf, respectively, when the frame is being worn. The CAM walker includes a collar assembly which is selectively fittable to, and manually separable from, the proximal end of the frame. As such, a medical practitioner, to address therapeutic needs, for example, may take actions with the CAM walker of this disclosure to fit the collar assembly to the proximal end of the frame; may forego attachment of the collar to the frame; or, if the collar were previously attached, may separate such collar from the frame, such as in response to other therapeutic needs.

The collar assembly has an engagement area which is oriented and configured so that, when it has been fitted to the frame, the engagement area engages, that is, contacts either directly or indirectly, the opposing surface of the other brace device which has been received in the CAM walker (and which brace device, in turn, is interposed between the collar assembly and the lower extremity received in the frame of the CAM walker).

In one variation of the implementations disclosed herein, the CAM walker frame has a foot bed with lateral and medial sides. The frame of the CAM walker, in turn, has corresponding lateral and medial frame elements which partially define a frame circumference and a corresponding frame volume, the circumference and volume being sufficient so that they are capable of receiving not only an ankle and corresponding lower extremity therein, but such ankle and lower extremity therein when wearing the other brace device received in the CAM walker.

The frame elements may include struts which extend upwardly from the foot bed on the lateral and medial sides and, in order to accommodate both the lower extremity and the surrounding brace device associated with the lower extremity, the struts are suitably transversely spaced to receive the other brace device therebetween, and yet also proximate to the opposing surface of the brace device to be engaged by portions of the collar assembly. In still further variations, the above-described collar assembly is selectively fittable to, and manually separable from, upper ends of the struts.

The collar assembly may be formed so as to include a pair of paddles of resilient polymeric material, along with at least one adjustable strap interconnecting such paddles. So, for example, the paddles each may have anterior and posterior side edges, and inner and outer surfaces, in which the inner surfaces have a pattern of inwardly extending protrusions formed thereon. The straps are positioned so that they extend between opposing edges of respective paddles and over outer surfaces of the paddles. In this way, when the straps are adjusted to decrease their circumference, a radially inward force is generated upon the paddles and as a result, the pattern of protrusions on the inner surface of the paddles engages the opposing surface of the brace device with suitable radially inwardly directed force.

The paddles may also be interconnected by means of a posterior brace member formed of resiliently flexible material and which extends between posterior edges of each of the pair of the paddles. In such configuration, the paddles are located on medial and lateral sides of the brace received in the frame of the CAM walker, with the posterior brace member extending and interconnecting the paddles from the posterior side.

In certain implementations, the engagement area defined by the collar assembly acts to extend the length of the lever arm formed during walking on the lower extremity, thereby reducing force on the planter surface of the foot when received in the CAM walker. Engagement of the collar assembly with the brace device may be suitably accomplished by having the engagement area of the collar assembly sized to engage at least 40% of the circumferential surface area of the opposing surface of the brace device.

In yet another potential implementation, the above-described engagement area may be comprised of inner surfaces of a pair of engagement members interconnected by at least one flexible strap, in which the engagement members each have an arcuate inner surface which extends in a concave arc of less than 45 degrees. The arcuate inner surface extends transversely to terminate an anterior and posterior longitudinal side edges. Extending from the respective anterior and posterior longitudinal side edges are engagement wings formed of resiliently flexible material. The resilient flexibility of the material forming the engagement wings is such that, when the strap is secured to the outside of the engagement members and their engagement wings, manual force not only transmits radial inward force from the strap to the engagement member, but also urges the engagement wings against the opposing surface of the brace device opposing the collar assembly.

The CAM walker and its associated collar assembly may be adapted so that the other brace receive in the CAM walker is in the form of a rigid or semi-rigid cast. In such implementation, the CAM walker has a frame with a circumference and volume to receive the cast therein.

Other objects, features and advantages of this disclosure will become apparent from consideration of the following detailed description and from the accompanying drawings, in which:

BRIEF DESCRIPTION OF THE DRAWINGS

FIG. 3 is a side elevational view of a portion of the collar assembly of FIGS. 1-2;

FIG. 4 is a side elevational view of the portion of the collar assembly shown in FIG. 3;

FIG. 5 is a rear elevational view of the portion of the collar assembly shown in FIGS. 3 and 4;

FIG. 6 is a top plan view of the portion of the collar assembly shown in FIGS. 3-5;

FIG. 7 is a bottom plan view of the portion of the collar assembly shown in FIGS. 3-6;

DETAILED DESCRIPTION

Figure 1:
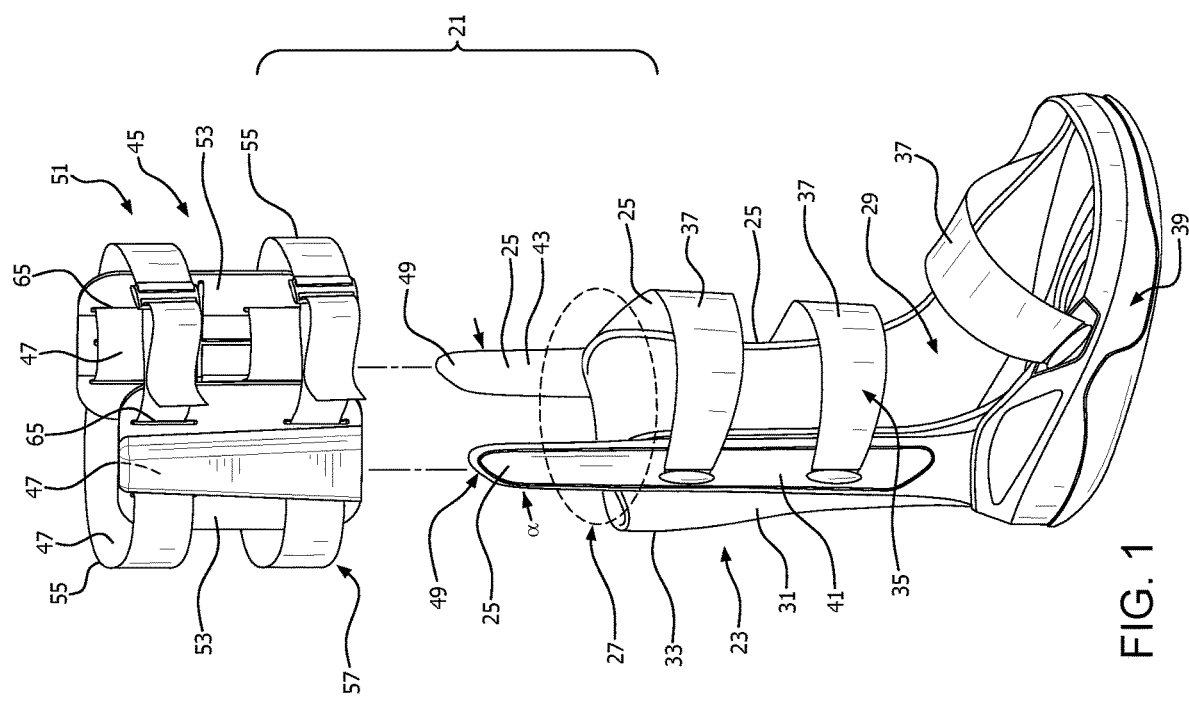
FIG. 1 is a perspective view of one possible implementation of a walker, such as a CAM walker, having a collar assembly which is removably attached to an underlying frame.

Referring more particularly to the drawings, FIG. 1 shows a perspective view of a walker 21 which is manually fittable to and removable from a lower extremity to be treated. In the illustrated embodiment, walker 21 is in the form of a CAM walker configured so as to be suitable for use with a brace device being worn by a patient, such as a cast, on his or her lower extremity. To that end, walker 21 includes a frame 23 which is not only adapted to control ankle movement of a lower extremity received thereon, but is also sized and shaped to receive both the patient's ankle and the associated brace device therein. To that end, frame 23 includes frame elements 25 which at least partially define a frame circumference 27 and a corresponding frame volume 29.

Frame elements 25 may assume a variety of configurations, including, for example, a rigid or resiliently flexible shell 31 having a posterior brace portion 33, a closure system 35, including one or more adjustable closure belts 37, a foot bed 39, and rigid or semi-rigid struts 41 extending upwardly or proximally (in relation to the wearer) from foot bed 39 on each of the lateral and medial sides of the foot bed. Struts 41 are transversely spaced by a distance a at their upper ends so as to have inner surfaces 43 proximate to opposing surfaces of the brace device (such as a cast) when worn on the lower extremity received in walker 21. Walker 21 as described herein is adaptable and suitable for use with any number or type of brace devices, whether rigid or semi-rigid casts of plaster, fiberglass, or alternate materials, splints, bandages or other removable bracing, and the like.

As such, frame 23 has an upper or proximal end adapted to operatively engage portions of the calf when received therein and a lower or distal end adapted to operatively engage portions of the foot, meaning to contact, directly or indirectly through the brace device, in order to protect, restrain, or otherwise control movement of the lower extremity for desired therapeutic purposes.

Figure 2:
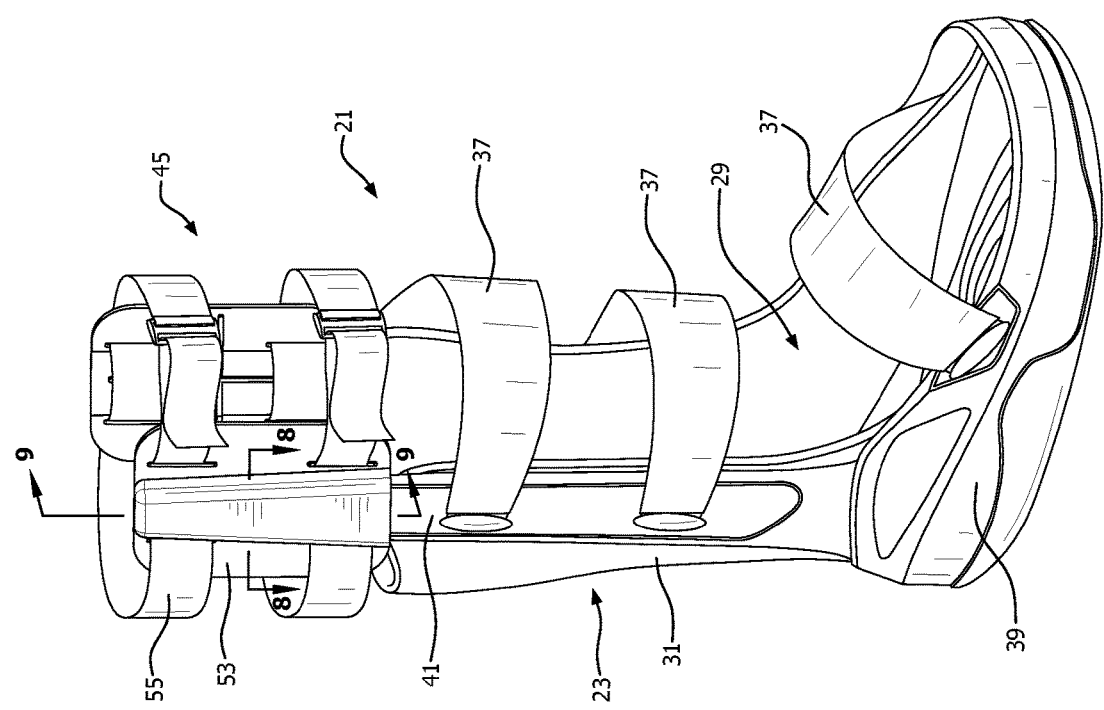
FIG. 2 is a perspective view of the walker of FIG. 1, with the collar assembly removably secured thereto.
Figure 8:
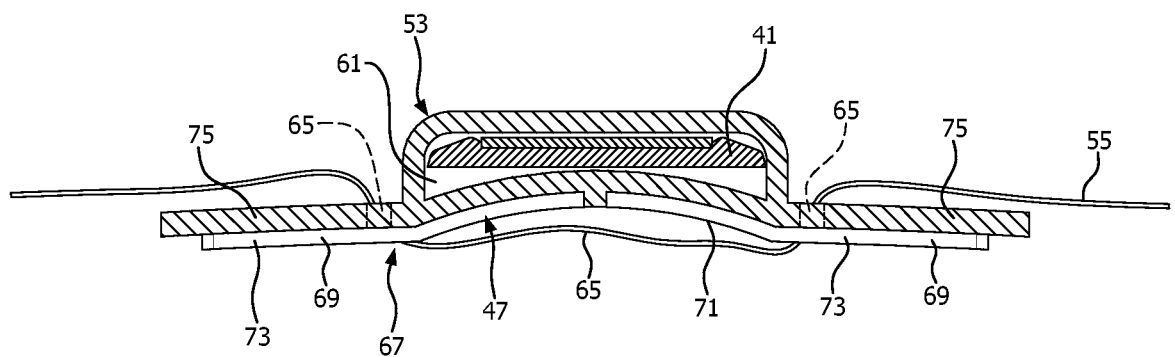
FIG. 8 is a sectional view taken along reference line 8-8 of FIG. 2.
Figure 9:
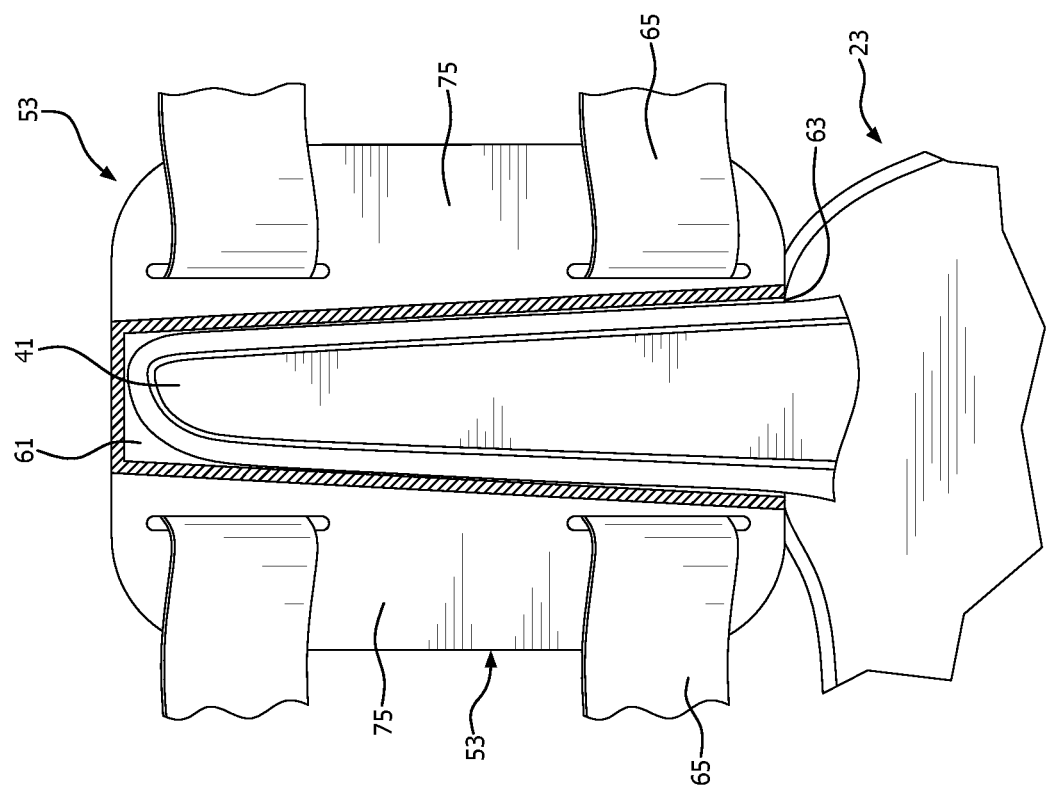
FIG. 9 is a sectional view taken along reference line 9-9 shown in FIG. 2.

In the disclosed and illustrated implementation, a collar assembly 45 is configured as subsequently detailed herein, so as to be selectively fittable to, and manually separable from, the proximal end of frame 23. FIG. 1 shows collar assembly 45 separated from frame 23, whereas FIG. 2 shows collar assembly 45 fitted to such frame 23. More particularly, collar assembly 45 is removably received on upper ends 49 of struts 41. Collar assembly 45 includes one or more engagement areas 47 oriented and suitably configured so that when collar assembly 45 has been fitted to upper ends 49 of struts 41, engagement areas 47 engage an opposing surface of the cast or other brace device received on or into frame 23.

Engagement area 47 may comprise inner surfaces of corresponding engagement members 53, and such engagement members 53 may assume any number of suitable forms, in the illustrated embodiments shown as paddles having quadrilateral profiles. Engagement members 53 are suitably interconnected or secured relative to each other by one or more adjustable, flexible straps 55 which make up a collar closure system 57 which can be manipulated to open or otherwise transform collar assembly 45 so it can surround the cast or other brace device associated with leg walker 21, and then adjusted, such as by tightening or shortening straps 55, thereby transmitting radially inward force on engagement area 47 of engagement members 53. Closure system 57 and associated straps 55 are oriented and sized so that manual tightening or other similar adjustment may produce sufficient inwardly directed force to substantially maintain the engagement of collar assembly 45 with the opposing portions of the cast during the anticipated gait cycle associated with the lower extremity and thereby impart to the patient all the advantages of such engagement.

Referring now to FIGS. 3-7, one of the engagement members 53 is shown in various plan views and described in further detail. Engagement member 53, shown as a paddle in the illustrations, has a longitudinal axis A and longitudinally extending connection portion 59 by which engagement member 53 can be removably secured to a corresponding one of struts 41 by longitudinal movement of connection portion 59 relative to strut 41 and its upper end 49. As best seen in FIG. 7, connection portion 59 is formed with inner surfaces defining a slot 61 which extends longitudinally and terminates in a slot opening 63 oriented distally or downwardly and sized to receive a mating portion of upper strut end 49 therein. Slot 61 and upper strut end 49 may be removably secured relative to each other by friction fit; mechanical interlock, such as with tabs or flanges, or press-fit or release mechanisms; fugitive adhesives, or hooks and eyes (VELCRO). Mating portions between collar assembly 45 and frame 23 may likewise take on different forms than slot 61 and upper strut end 49, including different configurations of male/female attachment or still other removable attachment structures.

Slits 65 extend through inner and outer surfaces of engagement member 53 so that corresponding straps 55 may be threadably received therethrough for operation as closure system 57 (FIGS. 1, 2).

Engagement member 53 includes opposite inner and outer surfaces, inner surface 67 being substantially planar but having formed thereon a pattern of protrusions 69 extending from inner surface 67, that is, away from the plane of such surface. When collar assembly 45 is secured to frame 23, protrusions 69 extend inwardly from the plan of inner surface 67 toward the corresponding opposing surface area of the brace device. Protrusions 69 are in the form of elongated elements or ribs 73 as illustrated, but may assume any number of shapes and patterns, including a roughed or stippled surface, a pattern of X's, O's, or the like, or any number of protrusions which terminate in surfaces having sufficiently narrow profiles so as to engage the opposing surface of the cast or other brace device corresponding to the upper surfaces of such protrusions 69. The combination of the area of inner surface 67 and geometries of the pattern of protrusions 69 are tuned or selected to substantially inhibit slippage of frame 23 relative to brace device received therein during ambulatory or other anticipated activity.

Inner surfaces 67 of engagement members 53 also include respective, arcuate, inner surfaces 71 which extend on such inner surface 69 to terminate in anterior and posterior longitudinal side edges and have concave arc β of less than 45°, and preferably have an arc extending between 10° and 30°. Extending from the longitudinal side edges of the arcuate surfaces 71 are engagement wings 75. Engagement wings 75 extend transversely, that is anteriorly and posteriorly, respectively, from the side edges of arcuate inner surface 71 and are formed of resiliently flexible material, with a resilient flexibility. Portions of straps 55 overlie or run along outer surface portions of engagement wings 75 so that, in response to straps 55 being adjusted or otherwise tightened and transmitting radially inward force, an inward force on outer surfaces of engagement wings 75, in turn, urges engagement wings 75 against the opposing surface of the brace device adjacent to collar assembly 45.

In view of the foregoing described structure, inner surfaces 67, including arcuate inner surface 71, inner surfaces of engagement wings 75, as well as inner surfaces of straps 55 (FIGS. 1, 2), together form the previously discussed engagement area 47. In this way, engagement members 53 interconnected by one or more of the straps 55 define a substantially cylindrical volume, which is not only sized to circumferentially receive the brace device therein, but is capable of transmitting radially inward force to the engagement area over substantially all of the 360 degrees of the circumference defined by the cylindrical engagement area 47.

The protrusions 29 which are urged by tightening of straps 55 radially inwardly are selected and configured so as to be suitable for engagement of rigid or semi-rigid cast material or other corresponding surfaces of the brace device received in CAM walker 21, and generally not suitable for direct contact with the skin of lower extremity received therein. By suitable engagement of the brace device by engagement area 47, engagement members 53 extend or lengthen the lever arm created between the distal end of CAM walker 21 and its proximal end. Since the frame 23 is configured to reduce force on the foot during gait as a function of the lever arm of CAM walker 21, the extension of the lever arm by addition of collar assembly 45 to frame 23 further reduces force on the plantar surface of the foot when received in CAM walker 21.

Operations of the walkers 21 described herein are apparent from the foregoing description. A medical practitioner or other user of walker 21 may choose to fit collar assembly 45 to frame 23 in order to achieve certain therapeutic goals. A lower extremity bearing a cast or other brace device is received in walker 21 within the volume defined by frame 23 and the circumferential volume defined by collar assembly 45. Suitable adjustment of one or more straps 55 or other comparable collar closure system caused inner surfaces of collar assembly 45 to define an engagement area 47. Such engagement area 47 is brought into engagement, either directly or indirectly with the brace device to help accomplish the desired therapeutic goal for the lower extremity received in the brace device, one such goal being to substantially inhibit movement of the casted lower extremity relative to walker 21.

In response to other therapeutic needs, CAM walker 21 may be used without collar assembly 45 received thereon, or after having removed such collar assembly 45 therefrom. In such cases, struts 41 and frame 23 may be suitably configured or structured so as to define a volume suitable for receiving a lower extremity without a cast or brace device therein. Suitable padding or other soft goods may be associated with frame 23 so that the volume of frame 23 is adapted to receive a lower extremity without a cast therein. As such. a treatment facility may simplify inventory and associated costs by having a frame 23 suitable for use both with non-casted lower extremities, without collar assembly 45 associated therewith, and with casted lower extremities, in which case collar assembly 45 would be fitted to frame 23.

In addition to the advantages apparent from the foregoing description, fixing the proximal portion of CAM walker 21 by means of engagement area 47 of collar assembly 45 allows the proximal portion of CAM walker 21 and the cast itself to move together in more unified movements during the gait cycle or other activities, limiting relative anterior and posterior movement of the cast relative to walker 21, having a positive effect on the gait pattern of the wearer to decrease undesirable forces on the foot, ankle, and lower leg which would otherwise interfere with therapeutic goals.

As a further advantage, the engagement member 53 enhances the offloading characteristics of leg walker 21, that is, reduces the force experienced on portions being treated by the cast on the lower extremity. As such, the combination of the collar assembly 45 and the frame 23 itself create increased mechanical support compared to either the cast itself, or a standard CAM walker.

The increase in lever arm by the collar assembly 45 along with underlying cast also serves to alter the wearer's gait to a more steppage style, thus distributing force over a larger contact surface area on the plantar surface of the foot. In a related manner, the alteration of gait limits speed and strain rate experienced by the foot and results in engagement of larger thigh muscles to advance the lower leg in gait and control the swing phase speed, thereby decreasing impact of the foot against the ground by virtue of engagement of the cast by collar assembly 45.

In one suitable implementation, foot bed 39 has an outer length (posterior to anterior) overall averaging about 315 mm as an outer dimension, and a medial-to-lateral outer dimension of about 140 mm (all such dimensions expressed herein suitably varying for gender, age, and size). Shell 31 of frame 23 extends upwardly or proximally at lateral and medial, respective locations which may be slightly inward of the outer width of foot bed 39. As such, distance a may range from about 140 mm (about 5½ inches) to about 114 mm (about 4½ inches). If the lateral and medial frame elements 25 include either struts 41 or semi-rigid or rigid material in shell 31, then corresponding inner surfaces 43 of struts 41 or shell 31 may define an inner diameter reduced by the thickness of such frame elements 25, such inner diameter ranging from about 75 mm (about 3 inches) to about 130 mm (about 5 inches). The frame elements 25 spaced as set out above may be used to define a diameter and thus a frame circumference 27 (FIG. 1) ranging from about 240 mm (about 9½ inches) to about 400 mm (about 15.7 inches). It will be appreciated that the transverse spacing of inner surfaces of frame elements 25, whether as part of shell 31 or struts 41 are selected to be spaced proximate to opposing surfaces of brace devices intended to be worn in the lower extremity, and thus the aforementioned dimensions may be further varied to suit particular applications of this disclosure.

Figure 10:
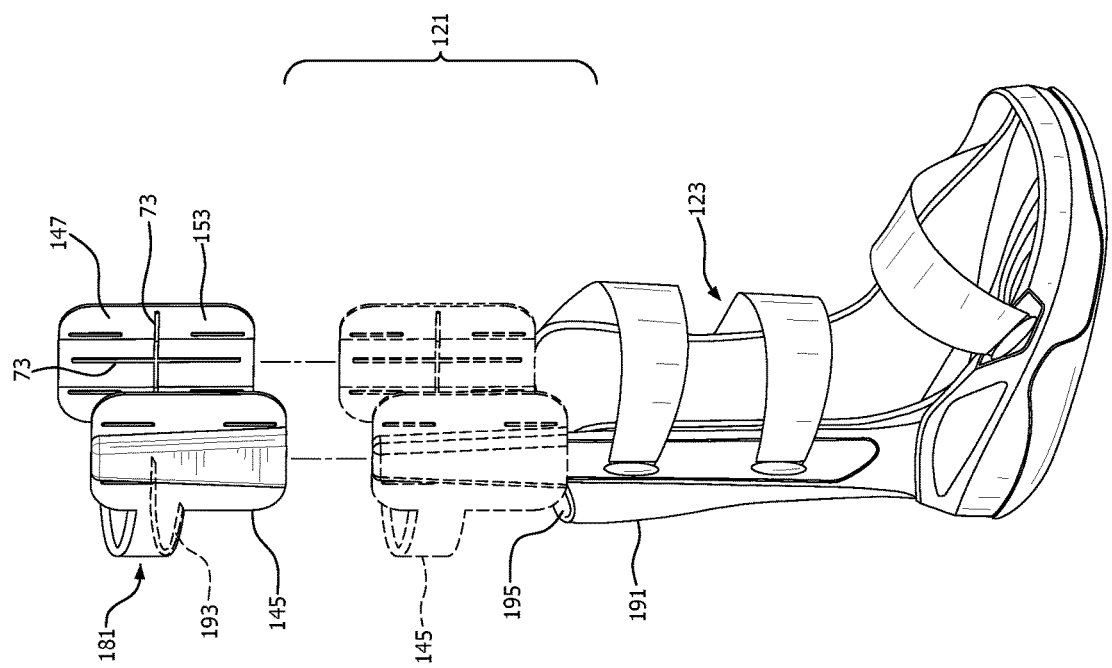
FIG. 10 is a perspective view of another possible implementation of this disclosure.

Proximal end of frame 23, as well as that of frames 123, 223 (described subsequently herein) may extend from a ground plane to corresponding upper proximal edges, such as corresponding to the upper edge of shell 39 below strut end 49 (FIGS. 1-9), or upper edges 195 (FIG. 10), 295 (FIG. 11), by a length ranging from about 230 mm (about 9 inches) to about 330 mm (about 13 inches), such lengths including the height of foot bed 39 and stated as an average height, recognizing that upper edge of frame 23 may be suitably contoured in a case of the illustrated embodiment of frame 23. The lengths of frame 23 may also correspond to the upper ends 49 of struts 41. Given the previously defined values for frame circumference 27 (and associated radii) and the aforementioned ranges in height of frame 23, the frame elements 25 define a corresponding frame volume 29 sized to receive both the ankle and the brace device therein, and ranging in volume from to 1,020 cm$^3$ to 4,380 cm$^3$.

Such dimensions have been found suitable to remain fixed relative to the underlying cast upon manual adjustment of Velcro-equipped straps having dimensions of between 12 mm and 25 mm (½ to 1 inch) in width. Upper ends 49 of struts 41 extend about 127 mm to 178 mm (about 5 to 7 inches) beyond the upper edge of shell 31. As such, if engagement at the upper end of shell 31 by uppermost one of straps 37 defines a lever arm for walker 21 having a first length, the addition of collar assembly 45 on the upper ends 49 of struts 41 increases the lever arm by about 127 mm to 178 mm (about 5 to 7 inches), thereby reducing force on the plantar service of the foot when received in walker 21. Engagement members 53 may be in the form of quadrilateral paddles, as illustrated, extending longitudinally between about 127 mm to 178 mm (5 inches and 7 inches) and transversely between about 100 mm to 152 mm (4 inches and 6 inches). Other sizes and dimensions are likewise suitable, depending on the brace device or other parameters and associated applications of the embodiments herein.

Still further variations are contemplated by this disclosure. Thus, for example, although protrusions 29 are described as engaging the opposing surface area of the cast or brace device received in walker 21, it will be appreciated that engagement area 47 may be equipped with adhesive materials, pneumatic arrangements, such as bladders, other friction inducing materials, hooks-and-eyes (VELCRO), ratchets, and other sorts of adhesive or mechanical affixation devices and materials, suitable for limiting anterior and posterior motion of the proximal end of leg walker 21 relative to the cast received therein.

Collar assembly 45 may likewise assume different configurations than the quadrilateral paddles shown here. For example, referring now to FIG. 10, another possible implementation has a leg walker 121 with removable collar assembly 145 including a posterior portion 181 formed of suitable resiliently flexible material to constitute or enhance a posterior brace and its associated functions on leg walker 121 and may likewise serve to interconnect lateral and medial paddle portions of engagement area 147 of engagement members 153. The removable attachment of collar assembly 145 shown in FIG. 10 may be accomplished in the manner similar to that described with reference to the implementations show in FIGS. 1-9. In addition, collar assembly 145 and proximal end of frame 123 may be formed so that posterior portion 181 mates with a corresponding posterior brace 191 on frame 123. In one possible version, posterior portion 181 includes a downwardly oriented slot 193, which receives an upper edge portion 195 of posterior brace 191 therein.

In still another possible implementation, a walker 221 includes a posterior ankle-foot orthosis ("AFO") 224 and an anterior AFO 226. Posterior AFO 224 is located to therapeutically engage the posterior portion of the lower extremity by contact through any bracing device therebetween. Anterior AFO 226 is removably secured to anterior locations of frame 223 of walker 221, so as to therapeutically engage the anterior portion of the extremity, such as the dorsum of the foot. The AFOs 224, 226 together form a "clam shell" arrangement. Anterior AFO 226 includes anterior reinforcing stay 228 extending longitudinally, that is, from proximal end 230 of frame 223 to distal end 232 of such frame 223.

Pairs of respective lateral and medial fingers 234 extend transversely from reinforcing stay 228 of anterior AFO 226, the pairs of fingers 234 located at spaced longitudinal locations on anterior AFO 226. Fingers 234 are located, sized, and configured to oppose corresponding portions on frame 223 so as to removably secure anterior AFO 226 relative to frame 223. In this particular implementation, hook-and-eye fasteners are used on opposing surfaces of frame portions 236 and fingers 234, such as fasteners marketed under the name VELCRO.

Figure 11:
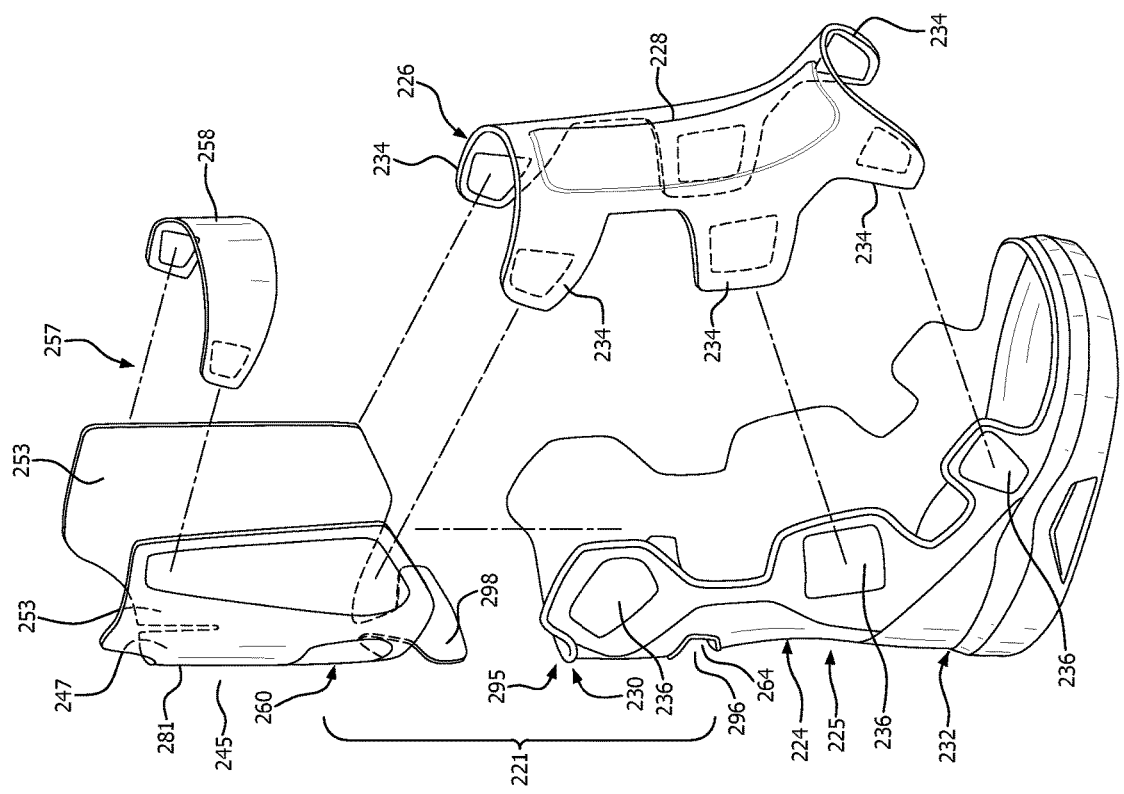
FIG. 11 is an exploded perspective view of still another possible implementation of this disclosure.
Figure 12:
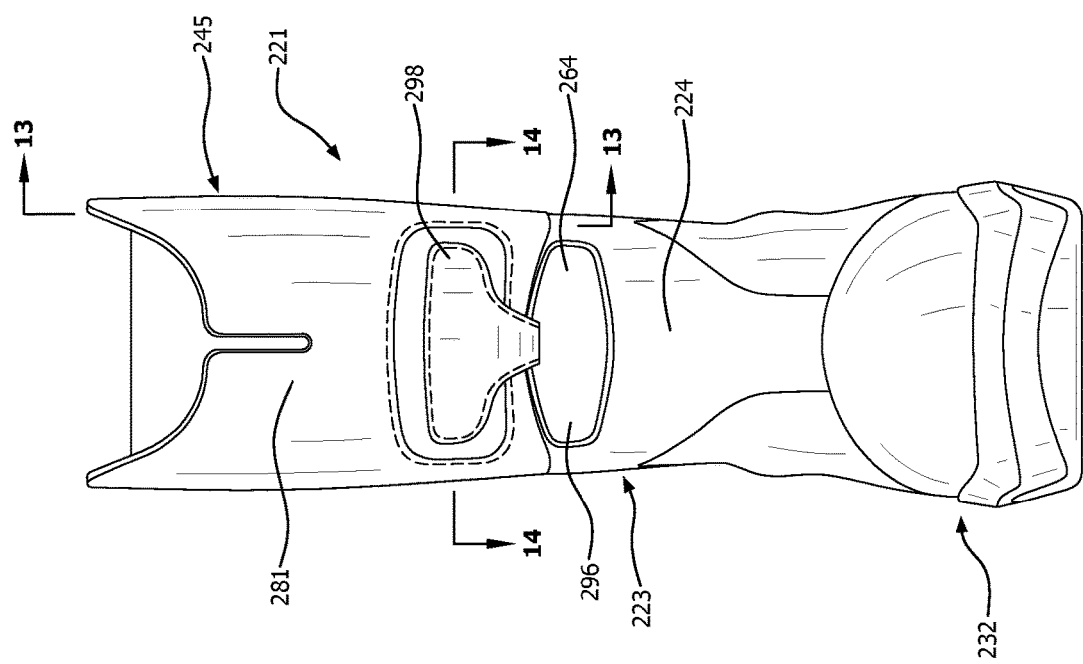
FIG. 12 is a rear elevational view of the implementation of FIG. 11.
Figure 13:
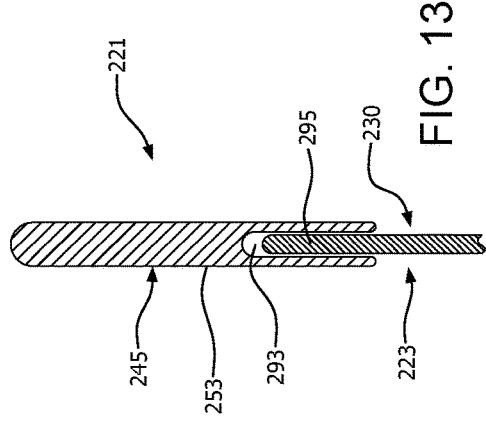
FIG. 13 is a cross-sectional view of the implementation of FIGS. 11-12, taken along line 13-13 of FIG. 12.
Figure 14:
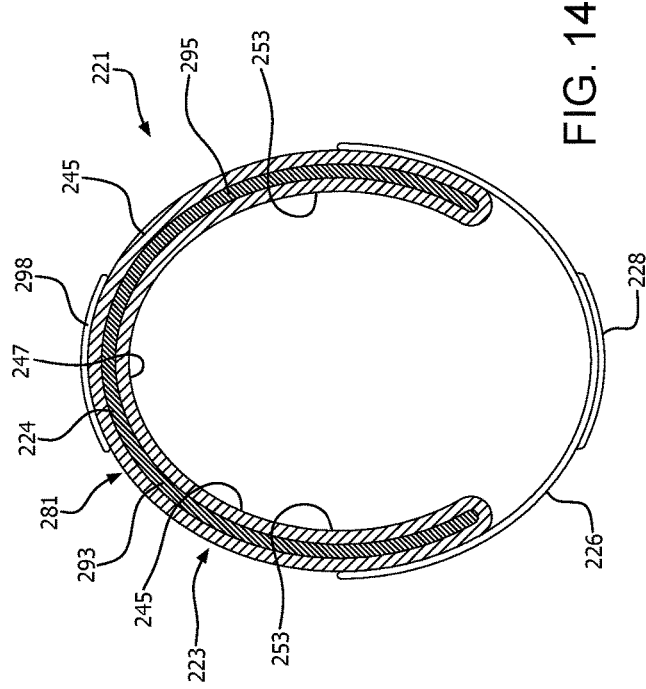
FIG. 14 is a cross-sectional view of the implementation of FIGS. 11-13, taken along line 14-14 of FIG. 12.

Walker 221 may include a removable or selectively fittable collar assembly 245, which operates on principles similar to those discussed with reference to collar assembly 45 and 145. FIG. 11 shows collar assembly 245 removed from frame 223, and FIGS. 12-14 show collar assembly 245 fitted to frame 223, to engage a brace device received in the frame volume defined by frame 223 and collar as discussed previously. In this implementation, collar closure system 257 makes use of a spacer 258 which may be removably secured, such as by hook-and-eye fasteners at its medial and lateral ends, to opposing medial and lateral portions of collar assembly 245.

Collar assembly 245 includes a posterior portion 281. Inner surface of posterior portion 281 may function to engage opposing portions of a brace device received therein and thus constitute one of several potential engagement areas 247. Extending from such posterior portion 281 are lateral and medial engagement members 253, each such members having corresponding inner surfaces which form additional engagement areas 247 for engaging opposing portions of a brace device received within collar assembly 245, as discussed previously in reference to the other embodiments. Engagement areas 247 may or may not include inner surface treatments, protrusions, or other features for enhancing engagement with opposing areas of the brace device received therein.

Collar assembly 245 in this implementation operatively engages opposing portions of the brace device received therein by urging engagement areas 247 radially inwardly and then securing such engagement areas 247 with suitable inward force, in this case with securing spacer 258. Securing spacer 258 extends between medial and lateral sides of collar assembly 245 and is removably secured at locations on the outer surface of engagement members 247.

The distal end portions 260 of collar assembly 245 are formed to define a downwardly oriented slot 293 sized and configured to receive therein upper end portion 295 of frame 223. In this implementation, slot 293 extends substantially around posterior portion 281 as well as the corresponding lower edges of medially and laterally located engagement members 253. The corresponding proximal end of frame 223 extends by a similar circumferential amount to be substantially received in the slot 293 as described.

Slot 293 extends proximally from the distal edge of collar assembly to define a slot depth of any suitable amount for collar assembly 245 to remain fitted to frame 223 and also extend the overall lever arm length of walker 221 if desired for therapeutic purposes. In one possible implementation, collar assembly 245 has an average (longitudinal) length of about 127 mm to 178 mm (5 to 7 inches), and slot 293 extends proximally, inwardly, along such length by amounts ranging from 20% to 70% of the collar assembly length. This results in engagement areas 247 of collar assembly 245 extending proximally beyond the upper (proximal) end 230 by corresponding amounts and extending the length of the lever arm created by walker 221 accordingly. For lever arms of walkers 121, 221 having a first length measured from ground plane to the upper, proximal ends 195 (FIG. 10), 295 (FIGS. 11-14), the dimensions and attachment of collar assemblies 145, 245 may be selected to increase the lever arm to a second length, the second length being longer by 25% to 60%, preferably about 30% to 40%. Other dimensions and configurations of slot 293 and edge portion 295 received therein are likewise suitable. Similarly, locations of slot or other mating portions of collar assembly and frame may be varied, such as by providing edge portion 295 with a slot for receiving an opposing edge (not shown) of the collar assembly 245 therein.

In the illustrated implementation, the proximal end of frame 223 has an aperture 296 formed therein which, among other potential functions, may serve as a handle 264 for manipulating walker 221, such as for fitting frame 223 to the lower extremity or removing it therefrom. Collar assembly 245 includes a tab 298 extending from an inner surface of the collar assembly, such surface located radially inwardly relative to slot 293. In this way, tab 298 is suitably located, dimensioned and configured to be foldable or moved hingedly so as to be selectively manipulatable around the upper edge of handle 264 formed in frame 223. Tab 298 further includes suitable fastening elements, such as hook-and-eye fasteners, so that, once manipulated around the upper edge of handle 264, tab 298 may be removably secured to the outer surface of collar assembly 245. In this manner, tab 298 restrains collar assembly 245 from proximal or upward movement relative to frame 223, because upward movement would cause tab 298 and upper edge of handle 264 to engage each other and thus resist proximal or upward movement of collar assembly 245.

Anterior AFO 226, collar assembly 245, spacer 258, and other components of walker 221 may be formed of any suitable resilient, flexible, rigid, or semi-rigid materials, possessing, corresponding reinforcing, resiliency, rigidity, of flexibility characteristics, in accordance with locations of such materials relative to a brace device received therein. Components formed from such materials would likewise have a certain amount of flexibility for purposes of operatively engaging corresponding portions of the lower extremity, either directly or indirectly through the brace device, thereby accomplishing immobilization, offloading, or other therapeutic objectives. As such, certain portions of frame 223 in collar assembly 245 are characterized as "semi-rigid," that is, resiliently flexible, the amount of resiliency and flexibility being tuned to the particular application.

Having described the various features and structures of the implementations of this disclosure, the scope of this disclosure is not confined to the details set forth and the patent is intended to include modifications and changes which may come within and extend from the following claims.

What is claimed is:

1. A CAM walker configured for use with a brace device, wherein the brace device is configured to be worn on a lower extremity of a user and received in the CAM walker, the CAM walker comprising:
   a frame comprising posterior and anterior portions, and configured to control ankle movement of the lower extremity, the frame having distal and proximal ends adapted to operatively engage portions of a foot and a calf, respectively; and
   a collar assembly configured to be selectively fittable to, and manually separable from, the proximal end of the frame; wherein the brace device is interposed between the collar assembly and the lower extremity when worn on the lower extremity and received in the frame of the CAM walker;
   wherein the collar assembly has an engagement area oriented and configured such that when the collar assembly is fitted to the proximal end of the frame, the engagement area contacts an opposing surface of the brace device;
   wherein the proximal end of the frame comprises a proximal edge and the collar assembly comprises a distally oriented slot adapted to receive the proximal edge of the frame therein when the collar assembly is fitted to the frame;
   the frame further comprising an aperture formed through the posterior portion of the proximal end of the frame, wherein the aperture is configured as a handle and is adapted to receive digits of the user of the CAM walker therein for fitting the frame to the lower extremity or removing it therefrom;
   the collar assembly further comprising a tab extending distally from an inner surface of the collar assembly, the inner surface located radially inwardly relative to the slot, wherein the tab includes fastening elements configured to be removably secured to cooperating fastening elements provided on an outer surface of the collar assembly, wherein the tab is dimensioned and configured to selectively extend through the aperture when the collar assembly is selectively fitted to the proximal end of the frame and is adapted to be foldable or moved hingedly so as to be selectively manipulatable around an upper edge of the handle formed in the frame such that, once manipulated around the upper edge of handle, the tab may be removably secured to the outer surface of the collar assembly via the fastening elements to restrain the collar assembly from proximal or upward movement relative to the frame.

2. The CAM walker of claim 1, wherein the collar assembly has a pair of resiliently flexible engagement members and at least one flexible strap interconnecting the pair of resiliently flexible engagement members, the pair of resiliently flexible engagement members and the at least one flexible strap having respective inner surfaces defining a substantially cylindrical volume having a circumference sized to circumferentially receive the brace device therein;
wherein the inner surfaces of the pair of resiliently flexible engagement members and the at least one flexible strap comprise the engagement area;
wherein the at least one flexible strap is adjustable to transmit a radially inward force on the engagement area over 360° of the circumference.

3. The CAM walker of claim 2, wherein each engagement member of the pair of resiliently flexible engagement members comprises an arcuate inner surface having opposite, anterior and posterior longitudinal side edges and a concave arc of less than 45° extending transversely between the side edges, wherein each engagement member of the pair of resiliently flexible engagement members has a pair of resiliently flexible engagement wings extending transversely from respective ones of the side edges of the arcuate inner surface;
wherein each of the engagement wings of the pair of resiliently flexible engagement wings has inner and outer wing surfaces;
wherein the at least one flexible strap is secured relative to the pair of resiliently flexible engagement members to have inner strap surfaces extending over the outer wing surfaces of each of the engagement wings;
wherein the resilient flexibility of each of the engagement wings is selected to urge the pair of resiliently flexible engagement wings against the opposing surface of the brace device in response to the at least one flexible strap transmitting the radially inward force.

4. The CAM walker of claim 3, wherein the engagement area comprises a quadrilateral paddle extending longitudinally between 3 inches and 7 inches and transversely between 4 inches and 6 inches and configured to remain fixed relative to the frame upon manual adjustment of the at least one flexible strap in response to forces caused by walking on the lower extremity when received in the CAM walker.

5. The CAM walker of claim 2, wherein the at least one flexible strap comprises two straps, the two straps extending anteriorly and posteriorly from anterior and posterior sides of respective ones of the pair of resiliently flexible engagement members.

6. The CAM walker of claim 2, wherein the frame has lateral and medial frame elements;
wherein each engagement member of the pair of resiliently flexible engagement members comprises a longitudinal axis and a longitudinally extending connection portion adapted to removably secure the engagement member to a corresponding one of the frame elements upon longitudinal movement of the connection portion relative to the corresponding frame element.

7. The CAM walker of claim 1,
wherein the frame comprises a foot bed having lateral and medial foot bed sides;
wherein the frame has lateral and medial frame elements partially defining a frame circumference and a corresponding frame volume sized to receive both an ankle and the brace device therein;
wherein the lateral and medial frame elements comprise struts extending upwardly from the foot bed on each of the lateral and medial foot bed sides;
wherein the struts are transversely spaced to be proximate to the opposing surface of the brace device when worn on the lower extremity;
wherein the struts terminate in respective, upper ends; and
wherein the collar assembly is configured to be selectively fittable to, and manually separable from, the upper ends of the struts.

8. The CAM walker of claim 7, wherein the collar assembly comprises a pair of paddles and at least one adjustable strap, each paddle of the pair of paddles having respective anterior and posterior edges and having inner and outer surfaces, the inner surfaces having a pattern of radially inwardly extending protrusions formed thereon, the at least one adjustable strap extending between opposing ones of the anterior and posterior edges of the paddles to interconnect the pair of paddles and define a collar circumference, the at least one adjustable strap extending over outer surfaces of each paddle of the pair of paddles so that, upon adjustment of the at least one adjustable strap to decrease the collar circumference, a radially inward force is generated, whereby the pattern of radially inwardly extending protrusions engages the opposing surface of the brace device with the radially inward force.

9. The CAM walker of claim 8, further comprising a posterior brace member of resiliently flexible material extending between the posterior edges of respective paddles.

10. The CAM walker of claim 1, wherein a distance between the distal and proximal ends of the frame defines a first lever arm having a first length, wherein the frame is configured to reduce force on the foot during gait as a function of the first lever arm, and wherein the engagement area is configured to extend to locations proximal to the proximal end of the frame and to engage the brace device at said locations to define a second lever arm having a second length greater than the first length, thereby reducing force on a plantar surface of the foot when received in the CAM walker.

11. The CAM walker of claim 1, wherein the engagement area of the collar assembly is adapted to engage opposing brace surfaces extending in a circumference defining a circumferential surface area, and is sized to engage at least 40% of the circumferential surface area of the opposing surface of the brace device.

12. The CAM walker of claim 1, wherein the collar assembly further comprises a collar closure system having portions configured for transmitting radially inward force on the engagement area of the collar assembly sufficient to substantially maintain an engagement of the brace device by the engagement area during a gait cycle associated with the lower extremity.

13. The CAM walker of claim 1, wherein the engagement area comprises a planar surface and a pattern of protrusions extending outwardly from the planar surface, the protrusions sized and oriented to engage the opposing surface of the brace device at locations corresponding to the protrusions.

14. The CAM walker of claim 1, wherein the brace device is selected from the group consisting of a cast, a splint, and a bandage.

15. The CAM walker of claim 1, wherein the frame further comprises:
- an anterior ankle-foot orthosis configured to be selectively fittable to, and manually removable from, the anterior portion of the frame;
- wherein the anterior ankle-foot orthosis comprises a longitudinally extending stay and at least one pair of transversely extending fingers; and
- wherein the at least one pair of transversely extending fingers comprise finger engagement areas; and
- wherein the proximal end of the frame comprises engagement portions located to oppose the finger engagement areas when the anterior ankle-foot orthosis is fitted to the frame.

* * * * *